(12) United States Patent
Schelling et al.

(10) Patent No.: US 8,759,569 B2
(45) Date of Patent: Jun. 24, 2014

(54) PROCESS FOR THE PRODUCTION OF ISOCYANATES, PREFERABLY DIISOCYANATES AND POLYISOCYANATES WITH SOLVENT RECIRCULATION

(75) Inventors: Heiner Schelling, Kirchheim (DE); Ulrich Penzel, Tettau (DE); Eckhard Stroefer, Mannheim (DE); Matthias Eiermann, Limburgerhof (DE); Jon S. Speier, Baton Rouge, LA (US); Kai Thiele, Antwerp (BE); Michael Bock, Ruppertsberg (DE)

(73) Assignee: BASF SE, Ludwigshafen (DE)

( * ) Notice: Subject to any disclaimer, the term of this patent is extended or adjusted under 35 U.S.C. 154(b) by 170 days.

(21) Appl. No.: 13/380,680
(22) PCT Filed: Jun. 16, 2010
(86) PCT No.: PCT/EP2010/058421
§ 371 (c)(1),
(2), (4) Date: Dec. 23, 2011
(87) PCT Pub. No.: WO2010/149544
PCT Pub. Date: Dec. 29, 2010

(65) Prior Publication Data
US 2012/0101299 A1    Apr. 26, 2012

Related U.S. Application Data
(60) Provisional application No. 61/220,740, filed on Jun. 26, 2009.

(51) Int. Cl.
C07C 263/00    (2006.01)
(52) U.S. Cl.
USPC ............................................ 560/347; 560/352
(58) Field of Classification Search
None
See application file for complete search history.

(56) References Cited

U.S. PATENT DOCUMENTS 6,576,788 B1 * 6/2003 Penzel et al. .................. 560/333
6,683,204 B1   1/2004 Stamm et al.
(Continued)

FOREIGN PATENT DOCUMENTS

| DE | 139 955 | 1/1980 |
|----|---------|--------|
| EP | 1 371 633 | 12/2003 |
| EP | 1 371 634 | 12/2003 |

OTHER PUBLICATIONS

Chem Systems, Process Evaluation Research Planning TDI/MDI 98/99S8 Tarrytown, N.Y., USA: Chem Systems, 1999, pp. 27-32 (Chem Systems) in view of U.S. Publication No. 20030230476 based on an application by Brady et al.*
Taurand, G., "Phenothiazine and Derivatives," Ullman's Encyclopedia of Industrial Chemistry. VCH Verlagsgesellschaft mbH, $5^{th}$ edition, vol. A19, pp. 387-401, (1991).
International Search Report Issued Jan. 24, 2011 in PCT/EP10/58421 Filed Jun. 16, 2010.

(Continued)

Primary Examiner — Karl J Puttlitz
(74) Attorney, Agent, or Firm — Oblon, Spivak, McClelland, Maier & Neustadt, L.L.P.

(57) ABSTRACT

The present invention relates to a process for the production of isocyanates, preferably diisocyanates and polyisocyanates of the diphenylmethane series (MDI), by reacting an amine with phosgene in the liquid phase or in the gas phase to form the corresponding isocyanates, subsequent removal of the solvent in at least two steps to obtain at least two solvent streams, individual treatment of the at least two solvent streams, and recirculation of at least a portion of the solvent streams.

20 Claims, 1 Drawing Sheet

(56) References Cited

U.S. PATENT DOCUMENTS

Figure 1:
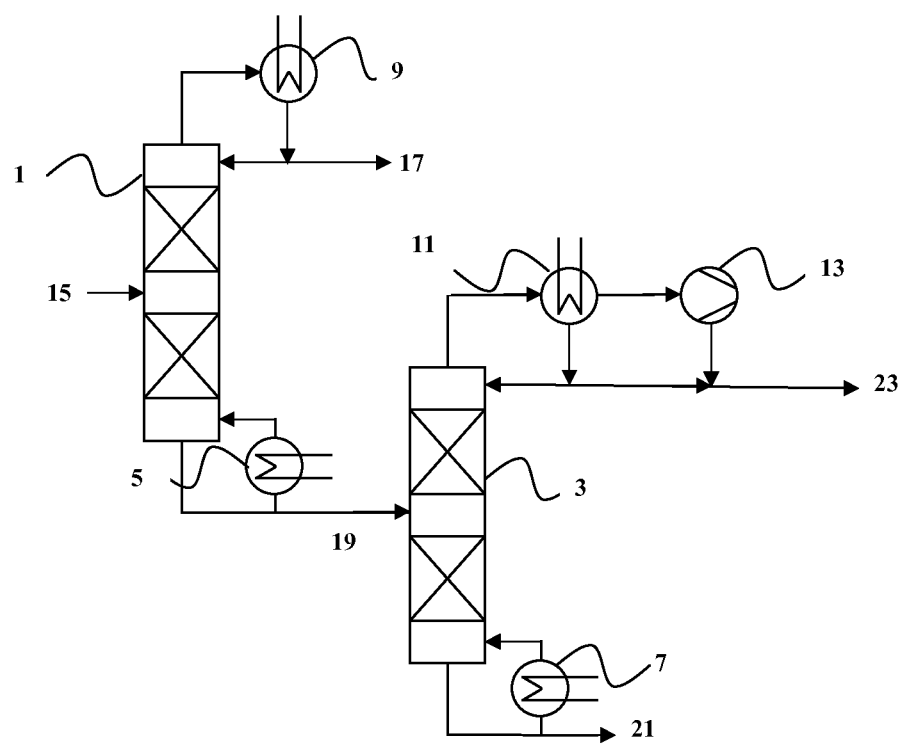

| | | | |
|---|---|---|---|
| 2003/0230476 A1* | 12/2003 | Brady et al. | 203/100 |
| 2005/0020797 A1* | 1/2005 | Pirkl et al. | 528/44 |
| 2010/0217035 A1 | 8/2010 | Knoesche et al. | |
| 2011/0021836 A1 | 1/2011 | Bock et al. | |
| 2011/0124908 A1 | 5/2011 | Rumpf et al. | |
| 2011/0251425 A1 | 10/2011 | Penzel et al. | |
| 2011/0263892 A1 | 10/2011 | Breuninger et al. | |
| 2011/0295039 A1 | 12/2011 | Raichle et al. | |
| 2011/0313192 A1 | 12/2011 | Rosendahl et al. | |
| 2012/0142960 A1 | 6/2012 | Bock et al. | |

OTHER PUBLICATIONS

U.S. Appl. No. 13/479,961, filed May 24, 2012, Stroefer, et al.
U.S. Appl. No. 13/299,039, filed Nov. 17, 2011, Bock, et al.
U.S. Appl. No. 13/298,851, filed Nov. 17, 2011, Bock, et al.
U.S. Appl. No. 13/383,549, filed Jan. 11, 2012, Schelling, et al.
U.S. Appl. No. 13/383,422, filed Jan. 11, 2012, Schelling, et al.
U.S. Appl. No. 13/501,621, filed Apr. 12, 2012, Franzke, et al.
U.S. Appl. No. 13/434,135, filed Mar. 29, 2012, Lehr, et al.

* cited by examiner

PROCESS FOR THE PRODUCTION OF ISOCYANATES, PREFERABLY DIISOCYANATES AND POLYISOCYANATES WITH SOLVENT RECIRCULATION

DESCRIPTION

The present invention relates to a process for the production of isocyanates, preferably diisocyanates and polyisocyanates of the diphenylmethane series (MDI), by reacting amine preferably dissolved in a solvent with phosgene to form the corresponding isocyanates, subsequent removal of the solvent in at least two steps to obtain at least two solvent streams, individual treatment of the at least two solvent streams, and recirculation of at least a portion of the solvent streams.

Various processes for preparing isocyanates by reaction of amines with phosgene are described in the literature. A solution of the amine in a suitable solvent is generally reacted with a solution of phosgene in the same solvent. Processes for the production of organic isocyanates from a primary amine and phosgene are described in the literature, for example in Ullmann's Encyclopedia of Industrial Chemistry, $5^{th}$ edition, volume A19, pages 390ff., VCH Verlagsgesellschaft mbH, Weinheim. U.S. Pat. No. 6,683,204 describes a process for the production of mixtures of monoisocyanates and oligoisocyanates by phosgenation of the corresponding amines in which a catalytic quantity of a monoisocyanate in an inert solvent is taken as an initial charge with phosgene. The amine, normally dissolved in solvent, is added and the reaction mixture obtained is reacted with phosgene. After an after-reaction step, excess phosgene and solvent are generally stripped out at temperatures from 30 to 80° C., condensed in a condenser and returned together to the after-reactor. However, no teaching on the required purity of the solvent can be derived from the teaching of this document.

U.S. Pat. No. 6,576,788 describes a process for producing mixtures of diphenylmethane diisocyanates and polyphenyl-polymethylene polyisocyanates (so-called polymeric MDI) by a two-step reaction of a mixture of the corresponding amines with phosgene in the presence of a solvent, maintaining selected ratios of phosgene and hydrogen chloride in the second process step. After the two-step reaction of the amine with phosgene in the solvent, the excess phosgene, the hydrogen chloride and the solvent are separated off from the reaction product (MDI) by distillation. Again, no teaching on the required purity of the circulating solvent can be derived.

Although it is not usually mentioned specifically in the literature of the prior art, it is generally known that the solvent that has been distilled off for the production of the amine and phosgene solution can be recirculated. The recirculation of the solvent that has been used in the synthesis of diisocyanate may be problematic for safety technology reasons. If water enters the system through, for example, a hole in a reaction tube which was caused or created by corrosion, the water reacts with the phosgene used as an educt in the isocyanate synthesis. Such a reaction between water and phosgene leads to the formation of hydrochloric acid, and this (i.e. hydrochloric acid) in turn may cause further corrosion problems in the plants.

Accordingly, it is an object of the invention to provide a process for the preparation of isocyanates using solvent recirculation, wherein amounts of impurities of water in the solvent used in the process are minimized. It is a further object of the invention to minimize corrosion effects in plants used for the preparation of isocyanates.

The inventors have found that this object is achieved by a process for the continuous preparation of isocyanates comprising
(a) preparing an isocyanate- and slovent-containing reaction solution by reacting an amine with phosgene using a solvent,
(b) separating crude isocyanate from the isocyanate and solvent-containing reaction solution at a pressure≥ambient pressure, preferred at a pressure of from 1 to 3 bar abs., more preferred of from 1 to 2 bar abs. to obtain a crude isocyanate stream and a first solvent stream,
(c) recycling at least a portion of the first solvent stream into the preparation step (a),
(d) separating the crude isocyanate stream to obtain a purified isocyanate stream and a second solvent stream at a pressure ≤ambient pressure, preferred at a pressure of from 0.005 bar abs. to 0.9 bar,
(e) optionally purifying at least a portion of the second solvent stream to obtain a second purified solvent stream having a water content of ≤100 ppm, preferably of ≤50 ppm, more particularly preferably of ≤20 ppm, based on the weight of the second purified solvent stream, and
(f) recycling at least a portion of the second purified solvent stream into the preparation step (a).

The inventors found out that impurities of water in the second solvent stream deriving from leakages of heat exchangers, sealings, flanges, vacuum devices and the like in an amount of ≥100 ppm, preferably of ≥50 ppm, more particularly preferably of ≥20 ppm may cause corrosion problems in the facility when this stream is recirculated without further purification, i.e. without removal of water.

According to an embodiment of the invention, the isocyanate and slovent-containing reaction solution is prepared in step (a) in the liquid phase comprising
(aa) producing a solution of an amine in a solvent,
(ab) providing phosgene, optionally as solution in the same solvent used to produce the solution of amine,
(ac) combining the solution of amine and the phosgene, and
(ad) reacting the amine in solution with the phosgene in solution to form the isocyanate and solvent containing reaction solution.

According to a further embodiment of the invention, the isocyanate and slovent-containing reaction solution is prepared in step (a) in the gas phase comprising
(aa') separately heating phosgene and the amine in vapour form, to a temperature of from 200° C. to 600° C. and continuously reacting phosgene with said amine in a reaction chamber,
(ab') passing the gas mixture which continuously leaves the reaction chamber through a solvent to obtain the isocyanate and solvent-containing reaction solution.

According to an embodiment of the invention, possible impurities of water in the second solvent stream are determined in step (e) and at least a portion of this stream is purified to obtain the second purified solvent stream having a water content of ≤100 ppm, preferably of ≤50 ppm, more particularly preferably of ≤20 ppm, based on the weight of the second purified solvent stream. After this, at least a portion of this second purified solvent stream is recycled into step (a), respectively into step (aa) and/or into step (ab) or into step (ab').

According to invention, a process for the continuous preparation of isocyanates is provided, wherein the solvent to be recycled is separated off from the isocyanate-containing reaction solution in at least two steps. In the first step process step (b) a first solvent stream is separated off from the reaction solution in a distillation column, a rectification column, a vaporization column, a crystallization tank, an extraction column or in combinations thereof at a pressure at a pressure≥ambient pressure and the first solvent stream is obtained. This first solvent stream usually contains about 90 to 99.5% by weight of the solvent to be recycled and about 0.5 to 10% by weight of so called light boilers such as HCl, phosgene and tetrachlormethane. As step (b) of the process of the invention is performed at a pressure ≥ambient pressure, leakage air will not enter into the system, and the content of water impurities in said first solvent stream is usually <100 ppm. Hence, this first solvent stream can usually be recirculated without further removal of the minimal traces of water.

According to a further preferred embodiment of the invention, the amount of impurities of water in the first solvent stream is monitored by means of a corrosion detection device, as disclosed in DD 139 955 and/or a mass spectrometer and/or a chromatographic system having a thermal conductivity detector (TCD), and, if the content of water is above 100 ppm, the first solvent stream is purified by means of a distillation column, a rectification column, a vaporization column, a crystallization tank, an extraction column or combinations thereof to obtain a first purified solvent stream having a polar solvent content of ≤100 ppm, preferably of ≤50 ppm, more particularely preferably of ≤20 ppm, based on the weight of the first purified solvent stream. This first optionally purified solvent stream is recycled into step (a), respectively into step (aa) and/or into step (ab) or into step (ab') of the process of the invention.

In step (d) of the inventive process, the crude isocyanate stream usually having an isocyanate content of from about 20 to 75% by weight and a solvent content of from about 25 to 78% by weight is separated in a distillation column, a rectification column, a vaporization column, a crystallizing tank, an extraction column or in combinations thereof at a pressure ≤ambient pressure, and a second solvent stream and an isocyanate stream are obtained. The solvent content of the second solvent stream is usually ≥98% by weight. As it is not avoidable that leakage air enters the vacuum equipment used in step (d) and causes condensation of water in the solvent, the second solvent stream contains a considerable amount of water, usually of from >100 ppm, based on the weight of the second purified solvent stream. Therefore, according to a preferred embodiment of the invention, the content of water in the second solvent stream is monitored by means of a corrosion detection device, as disclosed in DD 139 955 and/or a mass spectrometer and/or a chromatographic system having a thermal conductivity detector (TCD), and if the amount is above the threshold level of >100 ppm, based on the weight of the second solvent stream, at least a portion of the second solvent stream is purified to obtain a second purified solvent stream having a polar solvent content of ≤100 ppm, preferably of ≤50 ppm, more particularly preferably of ≤20 ppm, based on the weight of the second purified solvent stream. This second purified solvent stream is recycled into step (a), respectively into step (aa) and/or into step (ab) or into step (ab') of the process of the invention.

According to an embodiment of the invention the solvent streams to be recycled are monitored individually and if the content of water in the solvent stream is above the defined threshold level of 100 ppm, the streams are purified individually. Advantageously, this process allows the regeneration of the solvent refeeds in separate equipment, and minimizes the occurrence of corrosion. Since the first solvent stream is free of water, the hydrochloric acid contained in this stream cannot hydrolyse and cause corrosion problems in pipes and apparatuses used to guide and optionally purify this stream. Due to possible leakages in the vacuum devices or apparatuses used in step (d) of the inventive process, the second solvent stream may contain a certain amount of water which reacts with the phosgene when this solvent stream is recycled into a step (a). As the water content in this solvent stream is monitored permanently, and adjusted below the threshold level of 100 ppm, it can be recycled into step (a) without causing corrosion problems and leading to detectable formation of unwanted by-products.

As amines, it is in principle possible to use all primary amines which are able to react in an appropriate manner with phosgene to form isocyanates. All linear or branched, saturated or unsaturated aliphatic or cycloaliphatic or aromatic primary monoamines or polyamines which can be reacted with phosgene to form isocyanates are suitable in principle. Examples of suitable amines are 1,3-propylenediamine, 1,4-butylenediamine, 1,5-pentamethylenediamine, 1,6-hexamethylenediamine and the corresponding higher homologues of this series, isophoronediamine (IPDA), cyclohexylenediamine, cyclohexylamine, aniline, phenylenediamine, p-toluidine, 1,5-naphthylenediamine, 2,4- or 2,6-toluenediamine or mixtures thereof, 4,4'-, 2,4'- or 2,2'-diphenylmethanediamine or mixtures thereof, and also higher molecular weight isomeric, oligomeric or polymeric derivatives of the abovementioned amines and polyamines.

In a preferred embodiment of the present invention, the amines used are the isomeric primary diphenylmethanediamines (MDA) or their oligomeric or polymeric derivatives, i.e. the amines of the diphenylmethanediamine series. Diphenylmethanediamine and its oligomers or polymers are obtained, for example, by condensation of aniline with formaldehyde. Such oligoamines or polyamines or mixtures thereof are also used in a preferred embodiment of the invention. Further preferred amines are hexamethylenediamine, toluenediamine and isophoronediamine.

More preferred amines for the process of the present invention are the diamines and the polyamines of a diphenylmethane series (MDA, monomeric, oligomeric and polymeric amines), technical mixtures of 2,4- and 2,6-diaminotoluene (TDA, toluenediamines) in a weight ratio of 80 to 20, isophoronediamine and hexamethylenediamine.

The reaction of phosgene with the abovementioned amines can be carried out continuously or batchwise in one or more stages. The phosgenation produces the corresponding isocyanates, i.e. diisocyanatodiphenylmethane (MDI, monomeric, oligomeric and polymeric isocyanates), toluenediisocyanate (TDI), hexamethylenediisocyanate (HDI) and isophoronediisocyanate (IPDI). The process of the present invention is most preferably used for the production of the diisocyanates and polyisocyanates of a diphenylmethane series (MDI) and toluenediisocyanate (TDI).

The preparation of isocyanates taking place in step (a) in the process of the present invention is carried out in a manner known to those skilled in the art by reacting an amine or a mixture of two or more amines with a superstoichiometric amount of phosgene in the liquid phase or in the gas phase. It is in principle possible to employ all processes in which a primary amine or a mixture of two or more primary amines having one or more primary amino groups is reacted with phosgene to form one or more isocyanates having one or more isocyanate groups.

All solvents suitable for the use in the preparation of isocyanates can be used as solvent. These are preferably inert aromatic, aliphatic or alicyclic hydrocarbons or their halogenated derivatives. Examples of such solvents are aromatic compounds such as monochlorobenzene or dichlorobenzene, for example o-dichlorobenzene, toluene, xylenes, naphthalene derivatives such as tetralin or decalin, alkanes having from about 5 to about 12 carbon atoms, e.g. hexane, heptane, octane, nonane or decane, cycloalkanes such as cyclohexane, largely inert esters and ethers such as ethyl acetate or butyl acetate, tetrahydrofuran, phthalate esters, dioxane or diphenyl ether.

According to an embodiment of the invention, the reaction of the amine solution with the phosgene solution (step (ad)) generally takes place at temperatures of from 20 to 240° C. and under absolute pressures of 1 bar to 50 bar. It can be carried out in one or more steps, phosgene generally being employed in a stoichiometric excess. In step (ac) the amine solution and the phosgene solution are combined, preferably using static mixing elements or special dynamic mixing elements, and then passed in through one or more reaction zones in which the mixture reacts to form the desired isocyanate.

The optional separation step of residual phosgene and hydrogen chloride from the isocyanate and solvent containing reaction solution in step (ba) is preferably carried out in such a way that a dephosgenated crude isocyanate solution is obtained with a residual phosgene content of <100 ppm, preferably <10 ppm, based on the weight of the crude isocyanate solution According to a preferred embodiment of the invention the separation of the crude isocyanate solution by distillation takes place in a manner adapted to the respective boiling points of solvent and isocyanate in a multi-step distillation sequence distillation. Sequences of this type are known from the prior art and described, e.g., for TDI in EP-A 1371633 and EP-A 1371634.

According to the preferred case of the production of MDI using monochlorobenzene as the solvent, the separation by distillation can advantageously take place in such a way that the crude isocyanate solution is worked up in two steps into a bottoms product containing at least 95 wt. %, most preferably at least 97 wt. % of isocyanate, based on the weight of the isocyanate-containing stream, which is preferably then freed of low boiling materials in additional steps. In the first step, 60 to 90% of the solvent contained in the crude isocyanate solution is preferably separated off by distillation under absolute pressures of from above 1400 mbar and at bottom temperatures of from 110 to 170° C., the vapours being worked up in a distillation column with 5 to 20 separation stages and 10 to 30% reflux, so that a solvent-containing stream with a water content of <100 ppm, preferably <50 ppm, most preferably <10 ppm, based on the weight of the solventcontaining stream, is obtained. This so called first solvent stream can be recirculated back into step (a).

In the second purification step, the residual solvent is separated off to a residual content of 1 to 3 wt. % in the bottoms product under absolute pressures from 60 to 1400 mbar and at bottom temperatures of from 130 to 190° C. The vapours can also be worked up in a distillation column with 5 to 20 separation stages and 10 to 40% reflux, so that a second solvent-containing stream having certain water content is obtained. The content of water in the second solvent stream is monitored as described above and if the amount is above the threshold level of >100 ppm, based on the weight of the second solvent stream, at least a portion of the second solvent stream is purified to obtain a second purified solvent stream having a polar solvent content of <100 ppm, based on the weight of the second solvent stream, before this stream is recycled into step (a).

The process of the present invention is explained in more detail below with reference to the figures by way of example.

In FIG. 1 an example of the process of the present invention is illustrated schematically.

EXAMPLE 1

The figure shows a first and a second distillation column 1, 3 which are equipped with a reboiler 5, 7 and a condenser 9, 11. The second distillation column 3 is equipped with a vacuum pump 13. The reboiler can be any of the standard types commonly found in the chemical industry, including in part falling film evaporators, forced circulation evaporators, pool boiling (kettle) evaporators, natural circulation evaporators, etc. The condenser can be any of the types in common use in the chemical industry including co-current and counter-current (knock-back) condensers. The column can be equipped with any mass transfer internals that are in common use in the chemical industry. These include, in part, sieve trays, valve trays, fixed valve trays as well as structured or random distillation packing.

The phosgenation is performed according to the state of the art. The amine is reacted with phosgene preferably in the liquid phase in the presence of a solvent solution in the liquid phase or with phosgene directly in the gas phase with a solvent used in the quench cooling of said reaction.

Excess phosgene, hydrogen chloride and hydrolyzable chloride compounds such as tetrachlormethane are at least partly removed with methods known in the art.

The resulting crude distillation feed 15 comprises 20% to 80% by weight of the solvent and 20 to 60% by weight of the isocyanate light boilers like HCl, phosgene and tetra-chlormethane in amounts below 0.5% by weight.

The crude distillation feed 15 is fed to a first distillation column 1 that operates at an absolute pressure of <1.4 bar and at a bottom temperature of from 100° C. to 180° C. The first solvent stream 17 is separated off from the crude distillation stream 15 in this first column 1. The first solvent stream 17 comprises >95% by weight of solvent and <5% by weight of HCl, phosgene and tetrachlormethane. As the pressure in the first distillation column is >1.0 bar abs. leakage air and water will not enter into this column. Hence, the solvent-containing stream 17 is virtually free of traces of water or other polar protic solvents and can be recycled without further purification.

The isocyanate-containing stream 19 comprising 25 to 90% by weight of isocyanates and 10 to 75% by weight of solvent is fed into a second distillation column 3. The second distillation column 3 operates at an absolute pressure of from 60 to 900 mbar and at a bottom temperature of from 130 to 180° C. In the second distillation column 3 the (solvent free) purified isocyanate stream 21 is obtained as bottom product and the second solvent stream 23 is obtained as an overhead liquid product. As the second distillation column 3 operates at an absolute pressure of from 60 to 900 mbar, a pressure below ambient pressure, the second solvent stream 23 may contain traces of water caused by leakage air. Accordingly, the first solvent stream 17 and the second solvent stream 23 are treated separately prior recycling at least a portion of the first or second solvent stream.

The invention claimed is:
1. A process for the continuous preparation of producing an isocyanate, the process comprising:
(a) preparing an isocyanate and solvent-containing reaction solution by reacting at least one amine with phosgene in a solvent, to obtain a reaction solution comprising an isocyanate and solvent;

(b) separating crude isocyanate from the isocyanate and solvent-containing reaction solution at a pressure ≥ambient pressure, to obtain a crude isocyanate stream and a first solvent stream;

(c) recycling at least a portion of the first solvent stream into the reacting (a); and (d) separating the crude isocyanate stream at a pressure ≤ambient pressure, to obtain a purified isocyanate stream and a second solvent stream at a pressure ≤ambient pressure, (e) optionally purifying at least a portion of the second solvent stream to obtain a second purified solvent stream having a water content of ≤100 ppm, based on the weight of the second purified solvent stream, and (f) recycling at least a portion of the second purified solvent stream into step (a).

2. The process of claim 1, wherein the separating (b) is carried out at a pressure of from 1 to 3 bar abs.

3. The process of claim 1, wherein the separating (d) is carried out at a pressure of from 0.005 to 0.9 bar abs.

4. The process of claim 1, wherein the reacting (a) is performed in liquid phase and comprises:
(aa) combining a solution comprising the amine and the solvent with the phosgene; and
(ab) reacting the amine in the solution with the phosgene in solution to obtain the reaction solution.

5. The process of claim 1, wherein the reacting (a) is performed in gas phase and comprises:
(aa') separately heating the phosgene and the amine in vapor form to a temperature of from 200° C. to 600 ° C. and continuously reacting the phosgene with the amine in a reaction chamber, to obtain a gas mixture; and
(ab') passing the gas mixture continuously from the reaction chamber through the solvent, to obtain the isocyanate- and solvent containing reaction solution.

6. The process of claim 1, further comprising:
(e) determining a content of water in the second solvent stream and purifying at least a portion of the second solvent stream, to obtain a second purified solvent stream having a water content of ≤100 ppm, based on a weight of the second purified solvent stream; and
(f) recycling at least a portion of the second purified solvent stream into the reacting (a).

7. The process of claim 6, wherein the determining (e) is performed with at least one selected from the group consisting of a corrosion detection device, a mass spectrometer, and a chromatographic system having comprising a thermal conductivity detector.

8. The process of claim 1, further comprising, prior to (b):
(ba) separating hydrogen chloride and excess phosgene from the reaction solution.

9. The process of claim 6, wherein the purifying (e) is carried out in at least one selected from the group consisting of a distillation column, a rectification column, a vaporization column, a crystallization tank, and an extraction column.

10. The process of claim 1, wherein the solvent is at least one selected from the group consisting of chlorobenzene, dichlorobenzene, and toluene.

11. The process of claim 1, wherein the amine is at least one selected from the group consisting of a diphenylmethane diamine, a diphenylmethane polyamine, a mixture of 2,4-diaminotoluene and 2,6-diaminotoluene in a weight-ratio of 80 to 20, hexamethylenediamine, and isophoronediamine.

12. The process of claim 1, which is performed as a continuous process.

13. The process of claim 1, further comprising:
(aa) combining a first solution comprising the amine and the solvent with a second solution comprising the phosgene and the solvent; and
(ab) reacting the amine in the first solution with the phosgene in the second solution to obtain the reaction solution.

14. The process of claim 1, wherein the separating (b) is carried out at a pressure of from 1 to 2 bar abs.

15. The process of claim 6, wherein the second purified solvent stream has a water content of ≤50 ppm, based on the weight of the second purified solvent stream.

16. The process of claim 6, wherein the second purified solvent stream has a water content of ≤20 ppm, based on the weight of the second purified solvent stream.

17. The process of claim 1, wherein the amine is a diphenylmethane diamine.

18. The process of claim 1, wherein the amine is a diphenylmethane polyamine.

19. The process of claim 1, wherein the amine is a mixture of 2,4-diaminotoluene and 2,6-diaminotoluene in a weight-ratio of 80 to 20.

20. The process of claim 1, wherein the solvent is chlorobenzene.

* * * * *